United States Patent [19]
Browning et al.

[11] 4,390,784
[45] Jun. 28, 1983

[54] ONE PIECE ION ACCELERATOR FOR ION MOBILITY DETECTOR CELLS

[75] Inventors: David R. Browning, Reisterstown; Gordon R. Sims, Jr., Joppa; John C. Schmidt; David W. Sickenberger, both of Baltimore, all of Md.

[73] Assignee: The Bendix Corporation, Southfield, Mich.

[21] Appl. No.: 229,480

[22] Filed: Jan. 29, 1981

Related U.S. Application Data

[63] Continuation of Ser. No. 80,887, Oct. 1, 1979, abandoned.

[51] Int. Cl.³ ............................................. H01J 49/40
[52] U.S. Cl. .................................... 250/287; 250/286
[58] Field of Search ............... 250/282, 283, 285, 286, 250/287, 381, 382, 384, 385

[56] References Cited

U.S. PATENT DOCUMENTS 3,394,252 7/1968 Gohlke et al. ..................... 250/423
3,626,182 12/1971 Cohen ........................... 250/41.9 TF
3,697,748 10/1972 Cohen ................................ 250/282
4,119,851 10/1978 Castleman et al. ................ 250/382

Primary Examiner—Alfred E. Smith
Assistant Examiner—Carolyn E. Fields
Attorney, Agent, or Firm—W. G. Christoforo; Bruce L. Lamb

[57] ABSTRACT

The ion accelerator for an ion mobility detector cell is comprised of a ceramic tube coated inside with a thick film resistor composition across which a voltage potential difference is impressed to provide an ion accelerating electrical field gradient within the tube.

8 Claims, 4 Drawing Figures

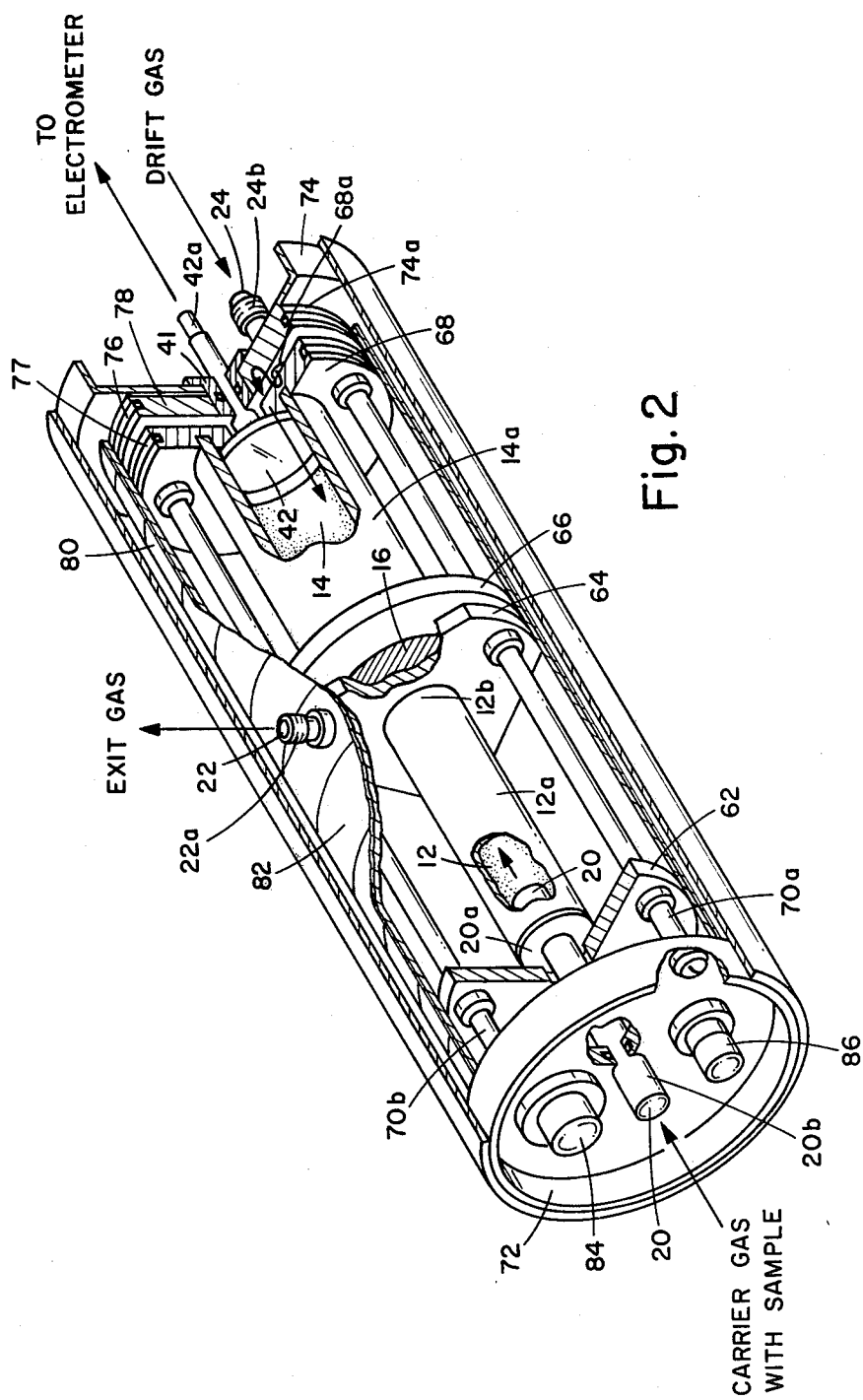

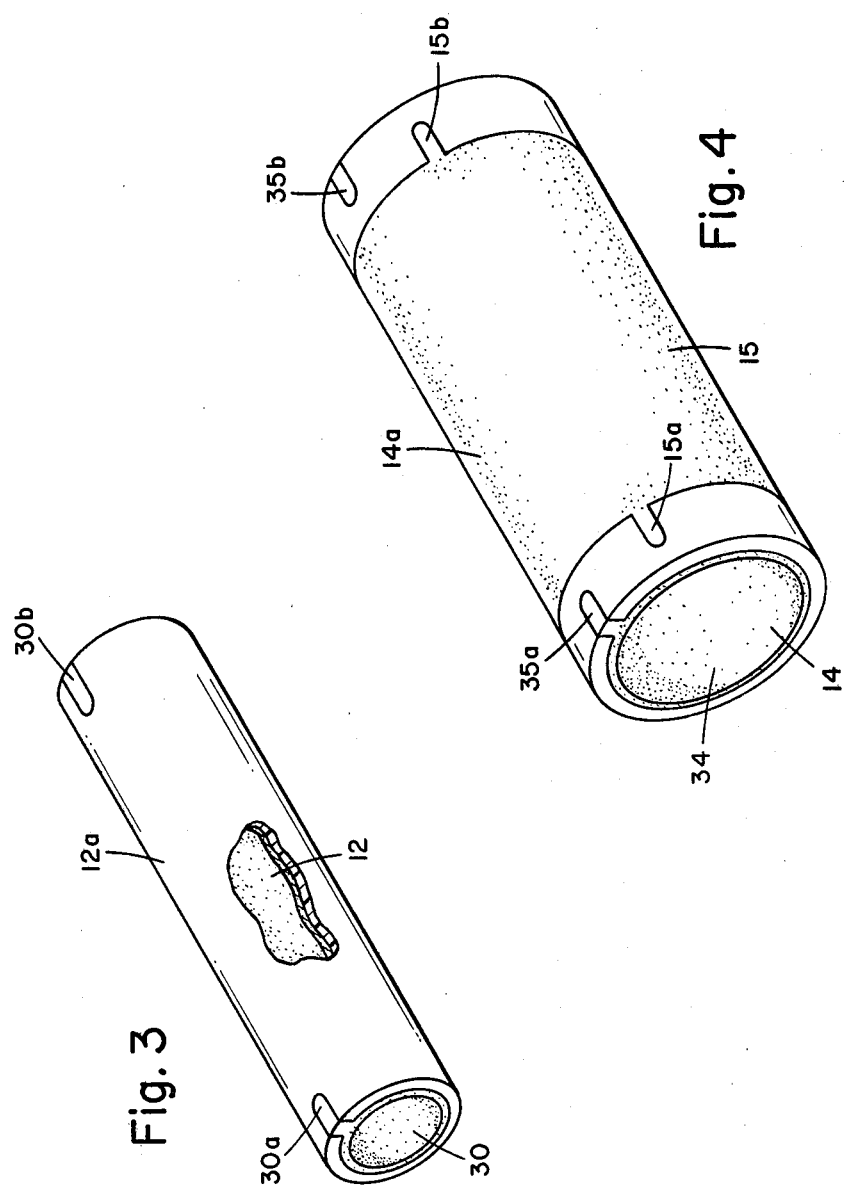

ONE PIECE ION ACCELERATOR FOR ION MOBILITY DETECTOR CELLS

This application is a continuation of application Ser. No. 80,887 filed Oct. 1, 1979, now abandoned.

FIELD OF THE INVENTION

This invention relates to ion mobility detectors and more particularly to the ion accelerating structure thereof.

BACKGROUND OF THE INVENTION

Ion mobility detectors are the primary instruments used in the field of plasma chromatography. Generally, the operation of an ion mobility detector is similar to the operation of a time of flight mass spectrometer, the obvious difference being that a time of flight mass spectrometer operates in a vacuum where the mean free path of the contained gases is many times the dimension of the gas container, while the ion mobility detector operates generally at atomspheric pressure where the mean free path of the contained gases is a small fraction of the dimensions of the container. More particularly, a typical ion mobility detector is comprised of a ionization source, an ion reactant region, an ion drift region and an ion injection shutter or grid interposed between the ion reactant region and the ion drift region. A carrier gas, normally purified atmospheric air, is introduced into the ion mobility detector with a gaseous sample of a material, whose identity is to be characterized by the ion mobility detector, so that the gaseous mixture is exposed to the ionization source. As a result, portions of both the carrier gas and the sample are directly ionized by the ionization source. However, as known to those practicing in this art, the characteristics of the carrier gas and the sample are usually such that the molecules of the carrier gas are more easily directly ionized by the ionization source than are the molecules of the sample. At this time the gaseous mixture is contained within the reactant region. Since the mean free path is many times smaller than the dimensions of the reactant region there are multiple collisions between the molecules of the carrier and sample gases. As also known to those skilled in the art, the tendency of these collisions is to transfer the ion charge from the carrier molecules to the sample molecules, thereby ionizing the sample gas mainly by this secondary ionization process.

The charged particles or ions, now mainly derived from the sample, are accelerated to a terminal velocity under the influence of a field potential gradient within the reactant region toward an ion injection grid which, as mentioned earlier, separates the reactant region from the drift region. The grid is normally electrically charged to prevent the transfer of ions from the reactant region to the drift region. Periodically, the grid is deenergized for a short time period to permit a pulse of ions to pass therethrough into the drift region. Here, the ions, under the influence of an electrostatic drift field are accelerated to an electrometer detector which terminates the drift region. The time of arrival of each ion at the electrometer detector, relative to the time the grid was opened, is determined by the ion's mobility through the non-ionized gas occupying the drift region. The heavier ions characteristically move more slowly through the drift region and arrive at the electrometer detector after longer drift times than lighter ions. It is thus possible to characterize the ions and hence, the sample by observing the time between the opening of the grid and the arrival at the electrometer detector.

In a practical sense, an ion mobility detector may be used to determine whether a certain sample is present in an environment, such as a certain contaminant in atmospheric air. In this case the electrometer detector is sampled at predetermined times after the grid is opened to discover whether pulses of ions are then arriving at the electrometer detector. If the proper combination of responses is obtained then it can be concluded that the contaminant is present.

In the prior art, the reactant region and the drift region are normally defined by the interior surfaces of tubular structures which are constructed of alternating electrically conductive and non-conducting rings. In the art, the conductive rings are termed guard rings. The region fields, above termed the field potential gradient in the case of the reactant region field and the electrostatic drift field in the case of the drift region, are generated by connecting adjacent guard rings through resistors and connecting the end rings respectively to the terminals of a voltage source. There thus results a series of conductive rings with ascending voltage levels impressed thereon so that the conductive rings, as interleaved with the non-conductive rings, comprise a tube having a longitudinal axis which coincides with the longitudinal axis of the above mentioned electrostatic field. It is believed in the prior art that the guard ring structure is needed to ensure an easily cleanable unit which is not apt to adsorb or absorb extraneous molecules which could cause erroneous responses.

SUMMARY OF THE INVENTION

The present invention comprises new, improved and less expensive means for generating the various electrostatic fields of an ion mobility detector. According to the present invention the fields are generated by a film resistor comprised of a film resistor composition disposed preferable on the inside of a non-conductive tube, such as a ceramic, glass, mullite, alumina or other suitable material tube and across which the proper voltage potential difference is impressed. One such tube is used to define the mobility detector reactant region and a second similar tube is used to define the drift region.

An operating ion mobility detector is normally heated above ambient to aid in desorbing unwanted molecules adhering to the interior surfaces thereof. Heating is effected by electrical heating tapes. Because of the prior art construction of ion mobility detectors wherein resistors interconnected the guard rings and the resistors were arranged along the exterior surfaces of the tube comprised of such guard rings, it was impossible to dispose the electrical heating elements directly onto the exterior surface of the guard ring structure. It was thus necessary to dispose the heating tapes on a separate structure which enclosed the guard ring structure. The present invention in eliminating the need for guard rings and their interconnecting resistors results in tubes which define the reactant and drift regions and whose exterior diameters are relatively smooth and clear. This allows the electrical heating tapes to be disposed directly on the tubes. With proper design, it is also possible to control the electrical resistance of the film resistor such that the required heat is developed directly on the inner surface of the tube where it is most needed.

It is the main object of this invention to provide the structure which defines the reactant and drift regions of an ion mobility detector and the applicable fields therein more economically than was available according to the prior art.

Another object of the invention is to provide an ion mobility detector having a heating element disposed on the inner or outer surface of the structure which defines the reactant and drift regions thereof.

A further object of the invention is to provide a film resistor which is used to generate the various electrostatic fields of and also heats the same ion mobility detector.

BRIEF DESCRIPTION OF THE DRAWINGS

FIG. 2 is an isometric view, cut away for clarity, of an ion mobility detector which incorporates the invention.

FIG. 3 is a detailed view of a conductor inlaid tube.

FIG. 4 shows a variation of the conductor inlaid tube of FIG. 2.

DESCRIPTION OF THE PREFERRED EMBODIMENT

Figure 1:
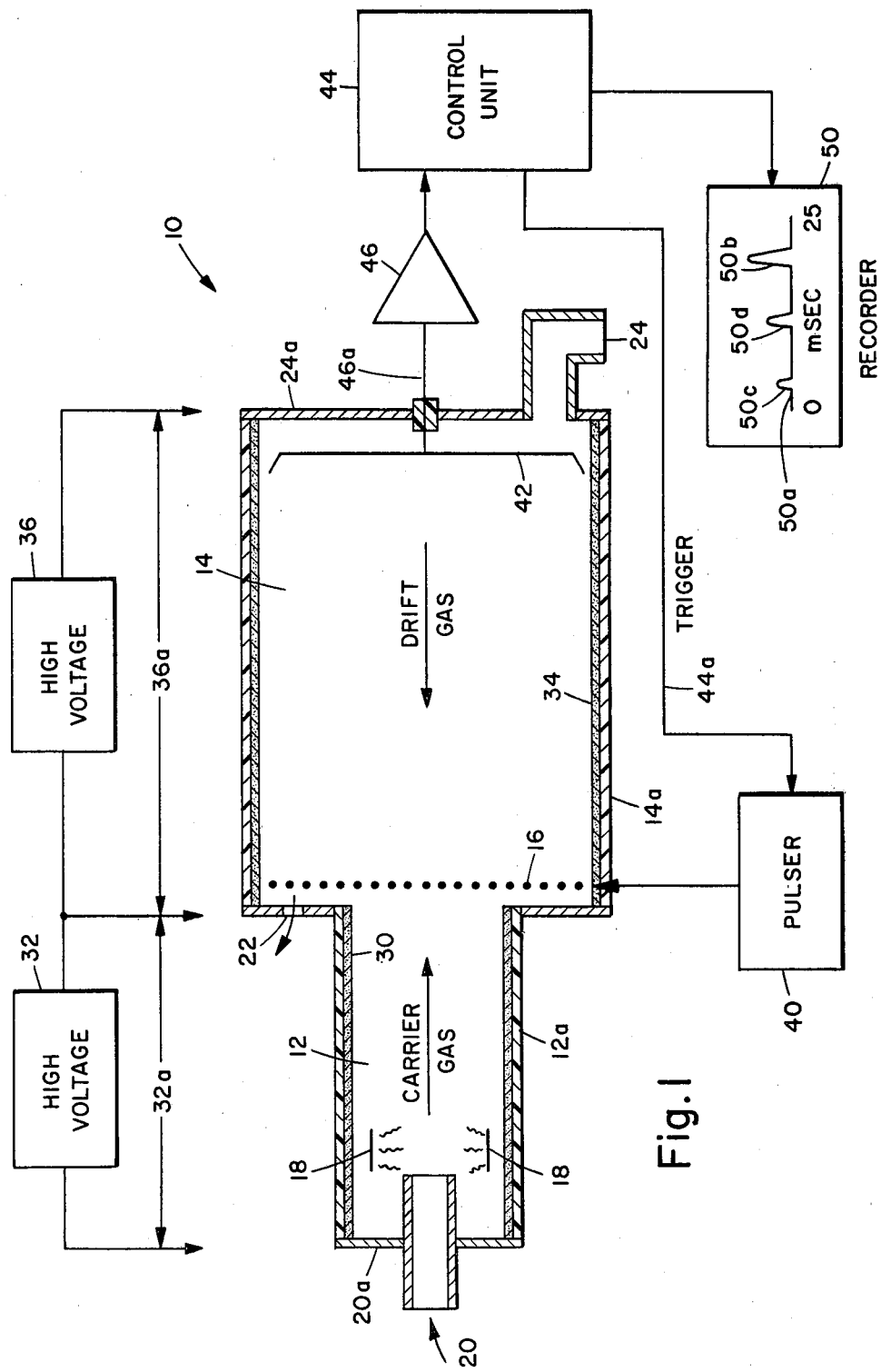
FIG. 1 is a block schematic diagram of an ion mobility detector constructed in accordance with the principles of the invention.

Referring first to FIG. 1, a typical ion mobility detector 10 is comprised of a reactant region 12, an ion drift region 14, an ion injection grid 16 located therebetween, and an ionization source 18. Reactant region 12 and ion drift region 14 are normally cylindrical in extent being defined by tubes 12a and 14a respectively. An inlet port 20 is provided in end wall 20a of reactant region 12 through which is injected to the reactant region a gaseous mixture comprised of a carrier gas, normally atmospheric air, and a sample of the gas which is to be characterized by the ion mobility detector. Another inlet port 24 is provided in end wall 24a of drift region 14 through which is injected a drift gas, also suitably purified atmospheric air, whose purpose will be described below. A vent 22 is provided from which the various gases are removed from the ion mobility detector. Any suitable means may be used to inject and remove the gases from the ion mobility detector. For example, a vacuum pump can be used at vent 22 to provide the means to remove the gases while atmospheric pressure provides the means to inject gases at ports 20 and 24. Of course, positive pressure means such as pumps can be used to inject gases at ports 20 and 24 with the gases being vented through vent 22 directly to atmosphere.

The gases injected at port 20 pass in close proximity to an ionizer such as ionization source 18, which is suitably nickel 63, a source of beta particles. Other ionizers such as tritium or a corona discharge might also be used. As previously mentioned, the beta particles primarily ionize the molecules of the carrier gas with some minor ionization of the sample being directly attributable to the ionization source beta particles.

Tube 12a which defines reactant region 12 is coated on its interior surface by a film resistance material 30 across which a voltage potential difference from high voltage source 32, and represented by 32a, is impressed thus causing a field potential gradient in tube 12a which accelerates the ions toward ion injector grid 16. The non-ionized molecules are carried along toward the grid 16 in the normal flow of gases toward vent 22. Since the ion mobility detector operates at atmospheric pressures, the mean free path of the ions and other molecules is very much less than the distance from inlet port 20 to grid 16. Thus, there are many collisions between the various gas molecules in reactant region 12. These collisions tend to create ionized sample molecules and deionize the previously ionized carrier gas molecules. The non-ionized molecules, mostly carrier gas molecules, are generally swept out of the ion mobility detector while the ionized molecules, mostly sample molecules, are trapped on the reactant region side of grid 16, which is usually electrically biased by pulser 40 to prevent the passage of ions, under the influence of the field generated by film resistor 30.

A control unit 44 includes an electronic clock which generates trigger pulses on line 44a which are applied to pulser 40. In response to a trigger pulse, pulser 40 generates a short pulse which is applied to grid 16 to bias the grid momentarily to pass a pulse of ions from reactant region 12 into drift region 14.

Tube 14a which defines drift region 14 has a thick film resistor 34 coated on its inside surface. A voltage potential difference represented by 36a and derived from high voltage source 36 is impressed across resistor 34 thus causing an electrostatic drift field in drift region 14 which accelerates the ions toward a faraday cup 42. The ions are accelerated in accordance with their mobility, the more mobile ions being accelerated faster and thus reaching faraday cup 42 before less mobile ions. The ions do not usually fall into a continuous mobility spectrum but rather tend to fall into discrete mobility groups. Thus, bundles of ions will reach faraday cup 42 at discrete times after grid 16 is pulsed with the time being related to the mobility of the ions in the bundle. The ions are deionized by the faraday cup, thus generating an electrical current on line 46a whose magnitude is related to the number of ions instantaneously striking the faraday cup. This current is amplified by amplifier 46 and applied to control unit 44.

As should now be obvious, the current signal from amplifier 46 is an ion mobility spectrum which can be plotted against a time base as shown at recorder 50 of FIG. 1. Of course, since the time is related to the mobilities of the ions, the time base can be calibrated in ion mobility. Thus, on the representative signal shown at 50a the spike at 50b indicates a large number of molecules of a certain mobility and lesser numbers of molecules of mobilities corresponding to time positions 50c and 50d.

In an ion mobility detector actually built, a single ion mobility spectrum was generated in 25 milliseconds by control unit 44 and included ions with masses from 1 to 400 amu. As known in the art, a convenient means to record such spectra is a digital signal averager which algebraically sums several hundred single spectra in a few seconds.

Not only the ions of the sample and carrier are passed through grid 16 into drift region but also non-ionized molecules of sample and carrier continuously migrate into the drift region. Under these conditions further ionizing of sample molecules might occur through collision of the sample molecules with air ions. Since this occurs some finite time after the original sample ions have been subject to the influence of the electrostatic drift field, this subsequent generation of sample ions will result in a broadening or smearing of the ion mobility spectra. The drift gas injected at port 24 hinders the formation of new sample ions in the drift region by sweeping non-ionized sample molecules out of the drift region and out through vent 22. In a practical ion mobility detector the flow of drift gas is several times the flow of the carrier and sample gaseous mixture.

Refer now to FIG. 2 where an ion mobility detector is seen cut-away for clarity. The construction of the ion mobility illustrated is identical or similar to the construction of known prior art ion mobility detectors except for the construction of tubes 12a and 14a, the purpose of FIG. 2 being to show the location of tubes 12a and 14a in an ion mobility detector rather than to describe the details of an ion mobility detector. Briefly, tube 12a, whose interior defines the reactant region 12, is supported between plates 62 and 64 while tube 14a, whose interior defines the drift region 14, is supported between plates 66 and 68. Tubes 12a and 14a are coaxial and gaseously communicate through grid 16, plates 64 and 66 having central bores (unseen) to allow such communication. Preferably, a standard ion mobility grid is contained between plates 64 and 66 in the conventional manner. Plates 62, 64, 66 and 68 are supported between flanges 72 and 74 by rods 70a, 70b and a third rod (not seen in this view) as illustrated. A tubulation 20b is held by crimpling into a central bore of flange 72. Tubulation 20b comprises port 20 through which the carrier gas and sample are injected into the ion mobility detector and also contains the ionization source 18 so that the injected gaseous mixture passed thereby.

Flange 74 supports and captures the stem 42a of a faraday cup 42 in an electrically insulating sleeve 41. Faraday cup 42 is connected to an electrometer as explained with respect to FIG. 1, through stem 42a.

The working elements of the ion mobility detector are contained within cylinder 80 which is supported by plates 62, 64, 66 and 68 and a boss 74a of flange 74. Boss 74a and plate 68 include annular grooves containing O-rings 76 and 77 respectively to form a relatively gas-tight chamber 78.

A spud 24b carried on flange 74 has a central bore which comprises port 24 through which the drift gas is injected into chamber 78 and thence through hole 68a and around faraday cup 42 into drift region 14 as described with respect to FIG. 1.

A spud 22a carried on cylinder 80 has a central bore which comprises port 22 shown also in FIG. 1.

Tape heaters 82 are wrapped on the exterior surface of cylinder 80 and are used to heat the operational portions of the ion mobility detector as shown in the prior art. The tape heaters, grid and the various ion mobility detector fields are electrically controlled through wires (not shown) which terminate at electrical connectors 84 and 86 in flange 72 in the conventional manner. As will be explained below, tape heaters 82 can be eliminated by proper design of the thin film to generate simultaneously the ion mobility detector electrostatic fields and the required heating. Alternatively, a separate thin film resistor may be disposed on the outer surface of the various tubes comprising the ion mobility detector and a power source may be connected thereacross to provide the required heating.

It should be particularly noted with respect to FIG. 2 that tubes 12a and 14a are continuous cylindrical structures rather than the cylindrical structures built up of a plurality of electrically conductive guard and insulating rings as in the prior art. It should also be noted that tubes 12a and 14a are very similar to one another except for size. Although both tubes are generally open ended, tube 12a is closed at its input end by a plug 20a, suitably of the same material as the tube and having a central bore to support tubulation 20.

Typical tube 12a is shown in FIG. 3, reference to which should now be made. Tube 12a is cut-away to show reactant region 12. The interior of the tube is coated with a continuous thick film resistor 30 across which a voltage potential, such as potential 32a of FIG. 1, is impressed. More particularly, thick film conductive tabs 30a and 30b are disposed on either end of tube 12a from the exterior surface thereof around the respective ends to communicate electrically with the opposite ends of thick film resistor 30. Potential 32a, for example, is impressed across resistor 30 at tabs 30a and 30b.

As previously noted, tubes 12a and 14a are very similar to one another. Both are made, preferably, of the same non-electrically conductive material. The preferable tube material is alumina. Other electrically insulating materials such as mullite, which is a high aluminum oxide/silicon dioxide material, ceramics, quartz, magnesium oxide, glass, etc., can also be used. Tabs 30a and 30b are preferably of platinum or gold. Other good electrical conductor materials such as silver, gold, platinum and even copper in some applications can also be used.

Resistor 30 (and resistor 34 of tube 14a) are preferably thick film printed resistors which are applied in a relatively liquid state and fired to form the thick film resistance. In the unit actually built the thick film resistors were BIROX (a trademark of the E. I. DuPont de Nemours & Co., Inc.) 9600-series resistor composition. This is a glass fritted resistance material which upon firing forms a resistor with a glass-like surface which is relatively hard, impervious to gas and easily cleaned. In this regard it makes an excellent material for use in an ion mobility detector since the outgassing and surface adsorption problems are minimized and cleanability is maximized. It might seem that if an overcoat of some dense material such as glass over the film resistor to improve cleanability and minimize outgassing would cause ions impinging on the overcoat to stick in the ionized state to the overcoat and neutralize and destroy the fields within the drift and reactant regions. This has not been the case in the present invention. Exactly why is not precisely known. It is believed that either the resultant glass-like surface is sufficiently conductive to allow the ions impinging on the interior of the tubes to be deionized and thus become ineffective in neutralizing the fields or else the ions do stick to the surface but repel like ions approaching the surface so that the net change in the field is negligible. The reason why the present invention is operative probably includes elements of both the above explanations.

In the unit actually built tube 12a was 3.75 inches long with an I.D. of 0.75 inches and an O.D. of 1.0 inch. A potential difference of 2000 volts was impressed across the tube (designated 32a in FIG. 1). Tube 14a was 3.25 inches long with an I.D. of 1.0 inch and an O.D. of 1.25 inches. A potential difference of 1500 volts was impressed across the tube. In both cases the resistance sheet resistivity was about 30 megohms per square.

Refer now to FIG. 4 which shows a further improvement of the invention illustrated with respect to tube 14a. It should be understood that the illustrated improvement is preferably used on tube 12a also if used on tube 14a. Tube 14a, like tube 12a, includes film resistor 34 coated on its interior surface and conductive tabs 35a and 35b. As previously noted, tube 14a defines drift region 14. The present improvement comprises a further film heating resistor 15 disposed on the outside tube surface and having conductive tabs 15a and 15b. It should be obvious that such resistance heaters when energized at tabs 15a and 15b by a suitable power source can be used in place of the tape heaters 82 of FIG. 2.

By proper design of the interior film resistor which generates the required electrostatic fields such as film resistor 30 of FIG. 3 or film resistor 34 of FIG. 4, that interior film resistor can also generate the required heat. If this is done not only is it possible to eliminate the tape heaters 82 of FIG. 2 but also the heating film resistor 15 exemplified by FIG. 4. For example, typically 2000 volts impressed across film resistor 34 of FIG. 4 will cause the required electrostatic field to be generated in tube 14a. Typically, 100 watts of heat is required for that tube. Thus, with 2000 volts impressed across tabs 35a and 35b and a film resistor having a resistance between these tabs of 40K ohms, film resistor 34 will provide both the required electrostatic field and heating.

Preferably the ion mobility detector electrostatic fields are continuous. Thus the film resistors generating those fields are usually continuous in the sense that they cover all or essentially all of the tube interior surface. It is possible for various applications to use what can be termed a relatively continuous film resistor in the sense that although the film resistor is electrically continuous between the terminals thereof it is not physically continuous in the sense that it describes a spiral or other specifically shaped film on the tube surface.

Other alterations and modifications of this invention should now be obvious to one skilled in the art after a reading and understanding of the foregoing. It is thus intended that the invention be limited by the true spirit and scope of the appended claims.

The invention claimed is:

1. In an ion mobility detector having an ion mobility grid and an enclosed volume in which an electrostatic field operates on ions for characterizing the mobility of said ions in said electrostatic field in an environment of gas and vapor molecules whose mean free path is many times smaller than the boundaries of said ion mobility detector, an improvement wherein the electrostatic field is enclosed within a relatively continuous structure comprised of first and second tubes communicating with each other through said ion mobility grid, said first tube encompassing a reactant region and said second tube encompassing a drift region, said relatively continuous structure having a film resistor disposed on the surface of said structure encompassing said field whereby a voltage potential difference impressed across said film resistor causes said field to be generated.

2. The improvement of claim 1 wherein said film resistor is disposed on the inside surface of said relatively continuous structure.

3. The improvement of claims 1 or 2 wherein the resistance of said film resistor is chosen to provide a predetermined power consumption by said film resistor when said potential difference is impressed thereacross.

4. The improvement of claims 1 or 2 wherein said relatively continuous structure is made of a dielectric material.

5. The improvement of claim 4 wherein said dielectric material is chosen from the group which includes alumina, mullite, ceramics, quartz, magnesium oxide and glass.

6. The improvement of claim 4 wherein said film resistor is made of a glass fritted resistance material fixed on said structure.

7. The improvement of claim 4 wherein said film resistor is characterized by a hard relatively gas impervious surface.

8. The improvement of claim 4 with additionally a relatively continuous film heating resistor coated on the exterior of said structure.

* * * * *